(12) United States Patent
Boehler et al.

(10) Patent No.: US 8,037,738 B2
(45) Date of Patent: Oct. 18, 2011

(54) PARTICULATE MATTER SENSOR

(75) Inventors: Jeffrey Boehler, Holland, OH (US);
Matthew B. Below, Findlay, OH (US);
Palani Thanigachalam, Bangalore
Karnataka (IN); **Ashutosh Kumar
Pandey, Bangalore Karnataka (IN); Jim
Cook, Freeport, IL (US); Tim Erickson**,
Mukwonago, WI (US); Steven Magee,
Lena, IL (US); Mike Rhodes, Richfield,
MN (US)

(73) Assignee: Fram Group IP LLC, Danbury, CT (US)

( * ) Notice: Subject to any disclaimer, the term of this patent is extended or adjusted under 35 U.S.C. 154(b) by 33 days.

(21) Appl. No.: 12/467,673

(22) Filed: May 18, 2009

(65) Prior Publication Data

US 2009/0301058 A1 Dec. 10, 2009

Related U.S. Application Data

(60) Provisional application No. 61/053,899, filed on May 16, 2008.

(51) Int. Cl.
*F01N 11/00* (2006.01)
*G01N 37/00* (2006.01)

(52) U.S. Cl. ........................................... 73/28.01

(58) Field of Classification Search ................ 73/23.3, 73/28.01, 114.71, 866.5
See application file for complete search history.

(56) References Cited

U.S. PATENT DOCUMENTS

| | | | |
|---|---|---|---|
| 3,438,241 A * | 4/1969 | McKinley, Jr. | 73/31.07 |
| 3,731,523 A * | 5/1973 | Vissers et al. | 73/19.05 |
| 3,942,546 A * | 3/1976 | Radd et al. | 137/93 |
| 3,977,232 A * | 8/1976 | Hickam et al. | 73/19.05 |
| 4,111,778 A * | 9/1978 | Davis et al. | 204/428 |
| 4,656,832 A * | 4/1987 | Yukihisa et al. | 60/303 |
| 4,716,874 A * | 1/1988 | Hilliard et al. | 123/406.14 |

(Continued)

FOREIGN PATENT DOCUMENTS

KR 20030094820 A 12/2003

(Continued)

OTHER PUBLICATIONS

International Search Report dated Dec. 28, 2009 for PCT/US2009/044351.

(Continued)

*Primary Examiner* — Lisa Caputo
*Assistant Examiner* — Punam Roy
(74) *Attorney, Agent, or Firm* — Cantor Colburn LLP

(57) ABSTRACT

Exemplary embodiments of the present invention relate methods and devices for measuring flow rate of particulate matter within an exhaust gas stream. In one particular exemplary embodiment, a sensor for detecting and monitoring particulate matter within an exhaust flow path of an engine is provided. The sensor includes a housing having an attachment for mounting the sensor. The sensor also includes a sensing rod supported by an insulating base. The sensing rod is attached to the housing and includes a probe adapted to be placed within the exhaust flow path. The probe includes a section having an increased surface area per unit length as compared to at least one other section of the probe. The sensing rod is configured to detect particulate matter flowing through the exhaust component and generates a signal based thereupon. The sensor further includes an electrical connector in communication with the sensing rod. The electrical connector is configured to transmit the signal generated by the sensing rod to a controller.

10 Claims, 8 Drawing Sheets

U.S. PATENT DOCUMENTS

| | | | |
|---|---|---|---|
| 5,071,532 A * | 12/1991 | Taillet et al. | 204/660 |
| 5,091,672 A * | 2/1992 | Below | 313/143 |
| 5,211,677 A * | 5/1993 | Sargeant et al. | 73/61.71 |
| 6,758,082 B2 | 7/2004 | Geier et al. | |
| 6,971,258 B2 * | 12/2005 | Rhodes et al. | 73/28.01 |
| 7,644,609 B2 * | 1/2010 | Reutiman et al. | 73/114.69 |
| 2004/0231315 A1 * | 11/2004 | Gonzalez | 60/202 |
| 2006/0090540 A1 * | 5/2006 | Gardiner | 73/23.33 |
| 2007/0068223 A1 * | 3/2007 | Chen et al. | 73/30.01 |
| 2007/0089399 A1 * | 4/2007 | Rhodes et al. | 60/278 |
| 2007/0089918 A1 * | 4/2007 | Gonzalez | 180/65.1 |
| 2007/0137177 A1 * | 6/2007 | Kittelson et al. | 60/277 |
| 2009/0113983 A1 * | 5/2009 | Krafthefer | 73/1.06 |
| 2009/0120164 A1 * | 5/2009 | Anilkumar et al. | 73/35.08 |
| 2009/0188300 A1 * | 7/2009 | Gualtieri et al. | 73/28.01 |
| 2010/0107737 A1 * | 5/2010 | Krafthefer et al. | 73/28.01 |

FOREIGN PATENT DOCUMENTS

| | | |
|---|---|---|
| WO | WO 9105994 A1 * | 5/1991 |
| WO | WO2007050384 A2 | 5/2007 |

OTHER PUBLICATIONS

Written Opinion of the International Searching Authority dated Dec. 28, 2009 for PCT/US2009/044351.

* cited by examiner

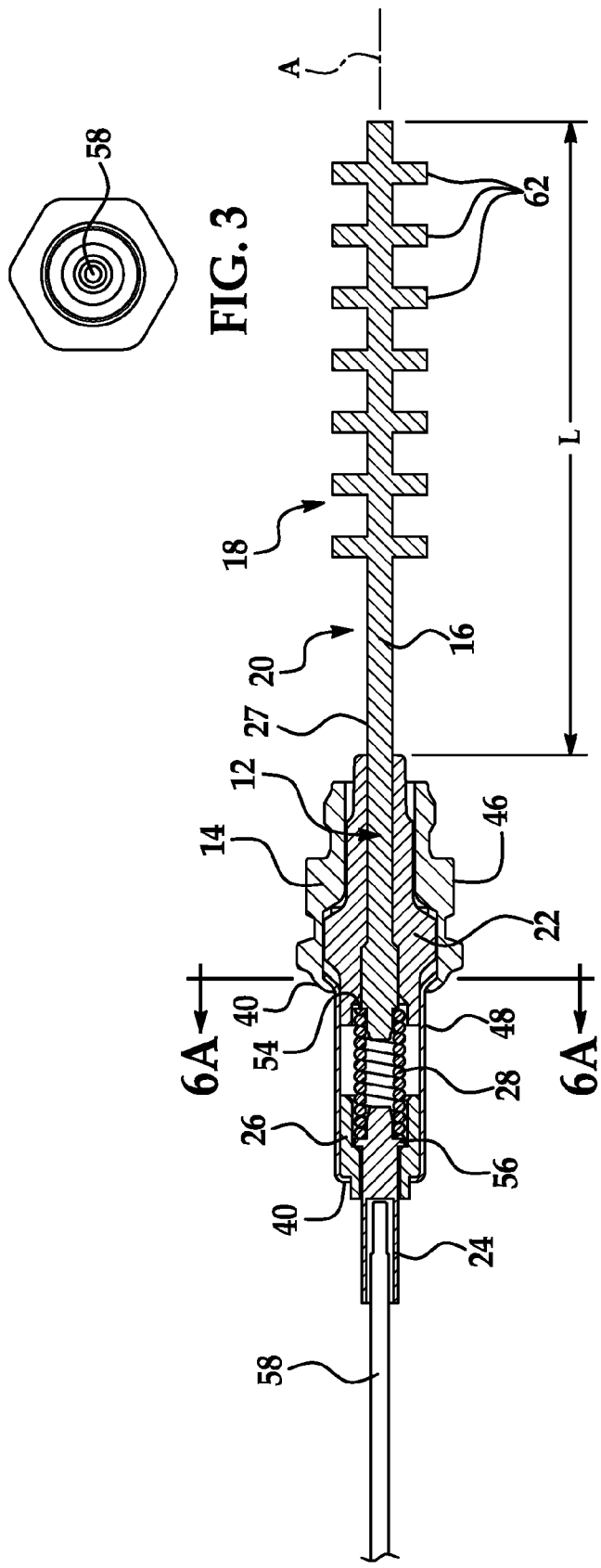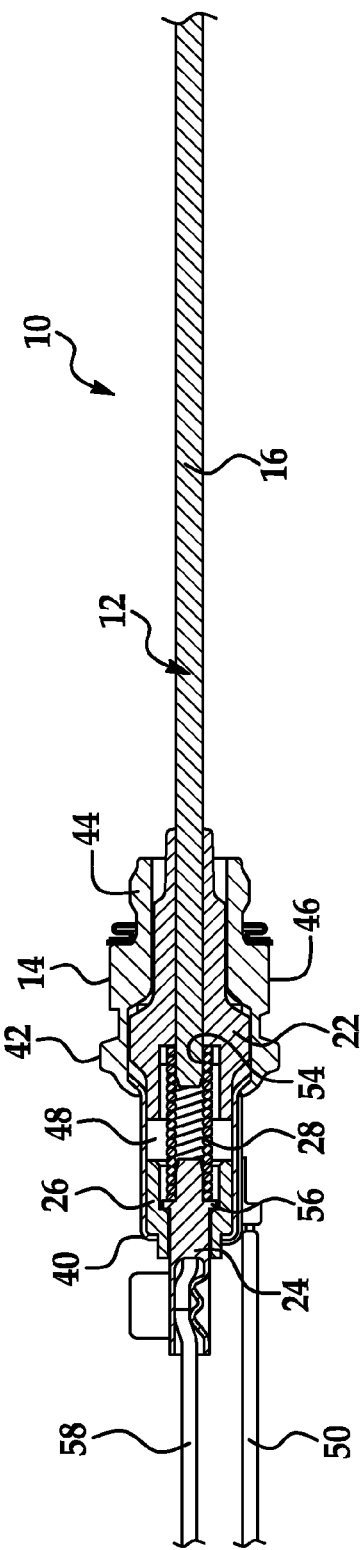

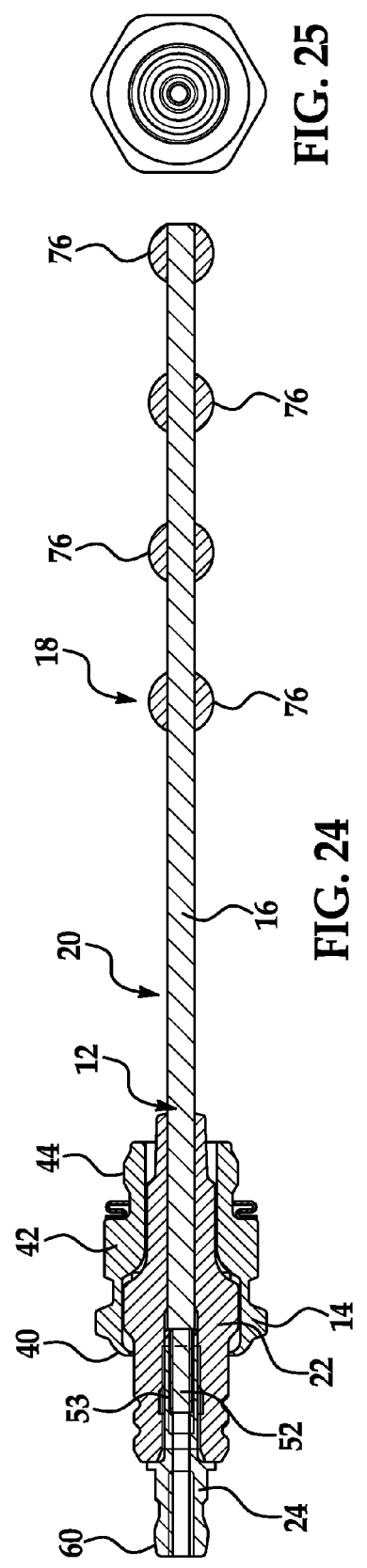
FIG. 24
FIG. 25
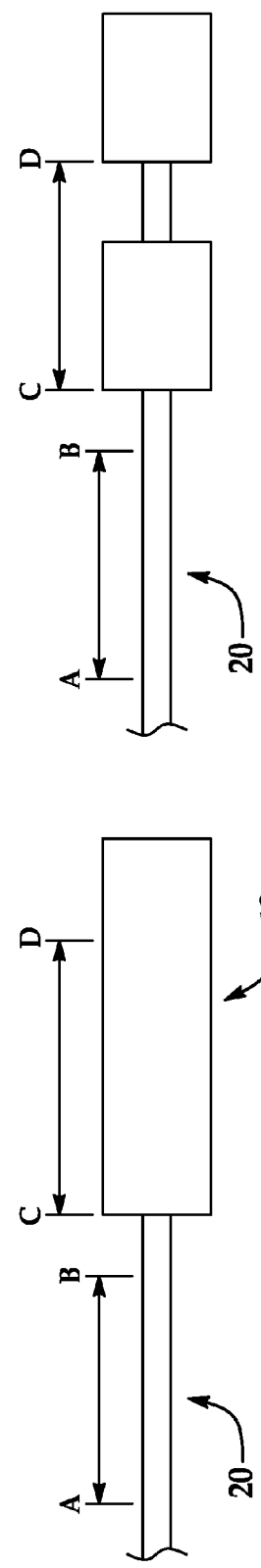
FIG. 26
FIG. 27
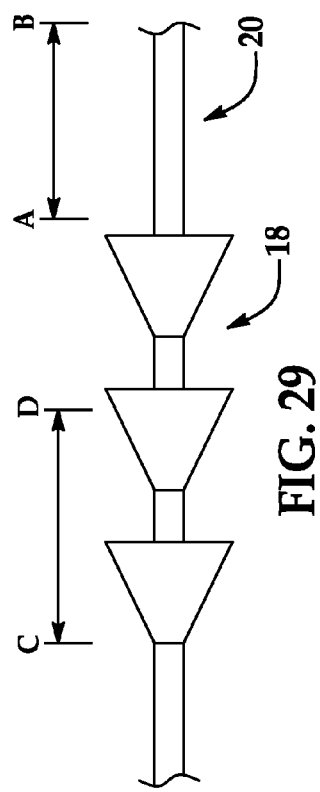
FIG. 29
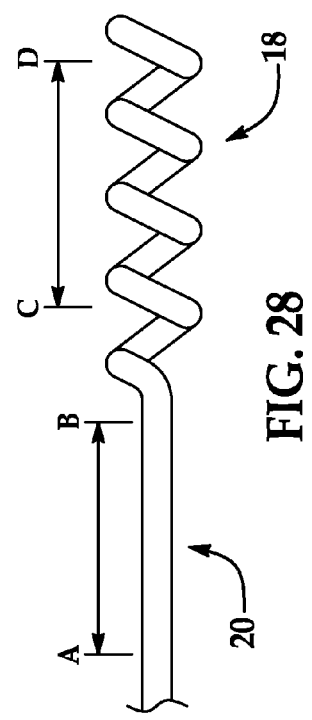
FIG. 28

PARTICULATE MATTER SENSOR

CROSS REFERENCE TO RELATED APPLICATIONS

This application claims the benefit of U.S. Provisional Patent Application Ser. No. 61/053,899 filed May 16, 2008, the contents of which are incorporated herein by reference thereto.

FIELD OF THE INVENTION

Exemplary embodiments of the present invention relate to methods and devices for monitoring the flow of particulate matter within an exhaust gas stream.

BACKGROUND

Emissions from stationary and mobile fossil burning devices have been and will continue to be of particular concern in view of accumulating laws and regulations restricting emissions from such devices. In one aspect, particulate matter within emission has been regulated causing industries, particularly the automotive industry, to utilize particulate matter removal devices. Such removal devices are configured to catch or trap particulate matter flowing through an exhaust gas stream prior to exiting an exhaust system of the emission generating device.

In another aspect, filters are used for removal of such particulate matter from exhaust gas streams, such as those generated by diesel engines, gasoline engines or otherwise. To determine when the particulate matter filter is reaching its capacity, the total volume or volume flow rate of particulate matter flowing into the filter or within the exhaust gas stream is monitored. This monitoring is often achieved through a particulate matter sensor exposed to the exhaust gas flow. In this configuration, the particulate matter sensor includes a probe extending into the exhaust gas flow. Some exhaust gas sensors function by transmitting signals based upon a resistance across the probe of the sensor for example, as particulate matter builds up across the sensor, the resistance changes thereby varying the output of the probe and accordingly providing an indication of the amount of particulate matter that has traveled past the sensor and into the filter.

However, many of these sensors fail to provide accurate readings of particulate matter flowing past the sensor or within an exhaust gas stream. For example, many of these sensors are not sufficiently robust to withstand forces or temperatures encountered by such sensors. Other problems with these sensors are their inability to accurately indicate the presence of particulate matter within an exhaust gas flow due to poor signal noise ratio and accumulation of particles on the sensor and other similar deficiencies. Still other problems exist as well.

Accordingly, in view of the shortcomings of previous sensor designs, as described above, there is a need for improved methods and devices for monitoring the flow of particulate matter flowing within and exhaust gas stream.

SUMMARY OF THE INVENTION

Exemplary embodiments of the present invention relate to methods and devices for measuring flow characteristics (eg., total volume, flow rate or otherwise) of particulate matter within an exhaust gas stream. In one particular exemplary embodiment, a sensor for detecting and monitoring particulate matter flowing within an exhaust gas flow path of an engine is provided. The sensor includes a housing having an attachment feature for mounting the sensor to a component. The sensor also includes a sensing rod supported by an insulating base. The sensing rod is attached to the housing and includes a probe adapted to be placed within the exhaust gas flow path. The probe includes a section having an increased surface area per unit length as compared to at least one other section of the probe. The sensing rod is configured to detect the amount of particulate matter that has flowed through the exhaust component and generate signals based thereupon. The sensor further includes an electrical connector in communication with the sensing rod. The electrical connector is configured to transmit the signals generated by the sensing rod to a controller.

In another particular exemplary embodiment, a sensor for detecting and monitoring particulate matter flowing within an exhaust gas flow path of an engine is provided. The sensor includes a housing having an attachment feature for mounting the sensor. The sensor also includes a sensing rod supported by an insulating base. The sensing rod is attached to the housing and includes a probe adapted to be placed within the exhaust gas flow path. The sensing rod is configured to detect the amount of particulate matter that has flowed through the exhaust component and generate signals based thereupon. The sensor further includes an electrical connector in communication with the sensing rod. The electrical connector is configured to transmit the signals generated by the sensing rod to a controller. The sensing rod also includes an electrically insulating layer comprising an oxide coating formed over the sensing rod, the electrically insulating layer providing electrical insulation between the sensing rod and the housing.

In still another particular exemplary embodiment, a method for determining flow characteristics (e.g., total volume, flow rate or otherwise) of particulate matter through an exhaust component of an engine is provided. The method includes placing a particulate matter sensor in an exhaust gas stream of an internal combustion engine. The particulate matter sensor includes a probe having at least one section with an increased surface area per unit length as compared to at least one other section of the probe. The method also includes determining the amount of particulate matter that has flowed past the probe.

In yet another particular exemplary embodiment, a method for determining flow characteristics (e.g., total volume, flow rate, or otherwise) of particulate matter through an exhaust component of an engine is provided. The method includes placing a particulate matter sensor in a exhaust gas stream from an internal combustion engine. The particulate matter sensor includes a sensing rod having an electrically insulating layer comprising an oxide coating formed over the sensing rod. The method further includes generating signals based upon the amount of particulate matter that has contacted the probe. The method also includes determining the amount of particulate matter that has flowed past the probe.

The above features and advantages and other features and advantages of the present invention are readily apparent from the following detailed description of the best modes for carrying out the invention when taken in connection with the accompanying drawings.

BRIEF DESCRIPTION OF THE DRAWINGS

Other objects, features, advantages and details appear, by way of example only, in the following detailed description of embodiments, the detailed description referring to the drawings in which:

FIG. 3 illustrates an end view of the sensor shown in FIG. 2;

FIG. 4 illustrates a cross sectional view of the sensor shown in FIG. 2;

FIG. 5 illustrates a cross sectional view of an alternate configuration of the sensor shown in FIG. 4;

FIG. 24 illustrates a cross sectional view of an eighth exemplary embodiment of a sensor according to the teachings of the present invention;

FIG. 25 illustrates an end view of the sensor shown in FIG. 24; and

FIGS. 26 through 29 illustrate various configurations of sensing rods according to exemplary embodiments of the present invention.

DETAILED DESCRIPTION OF EXEMPLARY EMBODIMENTS

Figure 1:
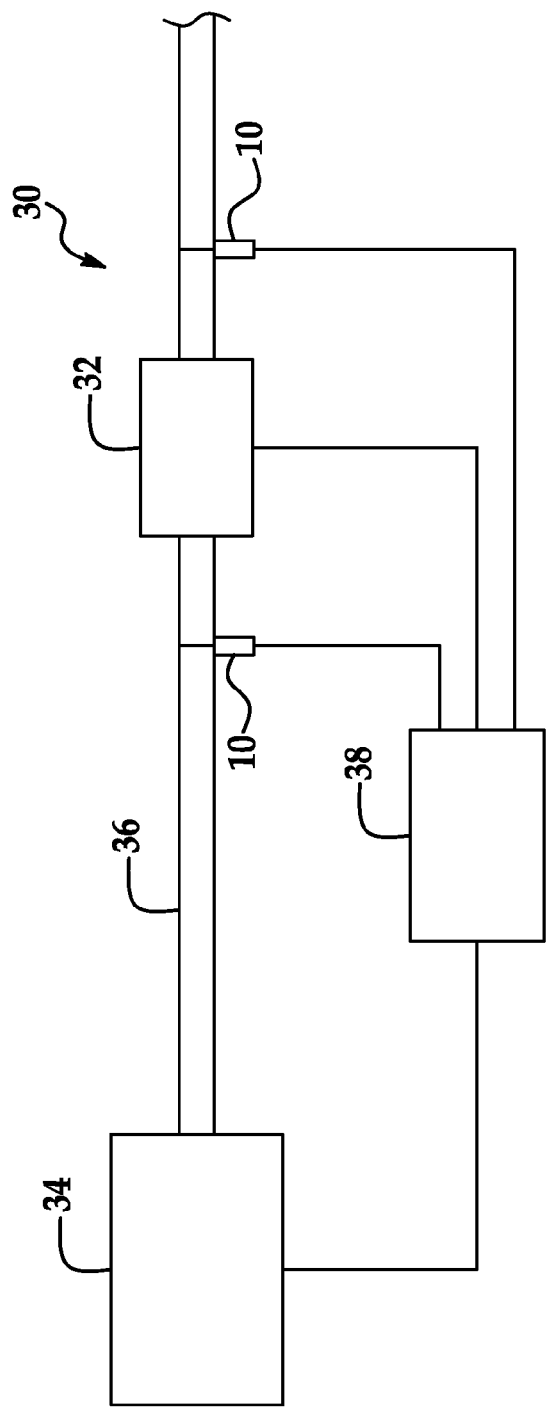
FIG. 1 illustrates a schematic view of an emission control system including one or more sensors according to an exemplary embodiment of the present invention.

Exemplary embodiments of the present invention provide methods, systems and devices for detecting and monitoring particulate matter flowing in an exhaust gas stream. In one particular exemplary embodiment, a particulate matter sensor is provided. The particulate matter sensor is configured for detecting and monitoring particulate matter flowing within an exhaust gas stream for determining volume or volume flow rate of particulate matter flowing within the stream. In certain configurations, sensors are provided having increased surface area for improving accuracy of detecting and monitoring particulate matter within the exhaust gas stream. In other configurations, particulate matter sensors provide improved robustness, reduction of components, reduction in cost or otherwise. Other advantageous will become apparent as shown and described herein.

Reference is made to the following U.S. Pat. Nos. 6,971,258; 7,275,415; and 4,111,778 the contents each of which are incorporated herein by reference thereto.

In general, referring to FIGS. 2-5 and 7-25, exemplary embodiments of improved particulate matter sensor assemblies 10 are provided. The sensor assemblies include a sensing rod 12 supported by a housing 14. The sensing rod includes a probe 16 configured for placement within an exhaust gas stream and for detecting particulate matter flowing within the stream. In one configuration, the probe includes a first section 18 having an increased surface area per unit length of the probe as compared to a second section 20 of the probe. The sensor assemblies further include a first insulator or insulating layer 22 for electrically insulating the sensing rod from the housing. The sensing rod is in communication with a device, such as a controller, through an electrical connector 24, which is also insulated from the housing through the first insulator or insulating layers or through a second insulator or insulating layer 26. In one configuration, the sensor assemblies may includes an intermediate connector 28 (such as a resilient member) for providing communication between the electrical connector and the sensing rod.

In one exemplary operation, referring to FIG. 1, an exhaust control system 30 is providing for monitoring and removing particulate matter from an exhaust gas stream. The exhaust control system includes and exhaust control device 32, such as a particulate matter filter, in fluid communication with an engine 34 through a suitable exhaust gas conduit 36. The exhaust control system also includes one or more sensor assemblies 10, such as particulate matter sensors, located before and/or after the exhaust control device. Of course the configuration and locations of the sensors of FIG. 1 are provided as non-limiting examples.

In one embodiment, as exhaust gas flows through the exhaust gas conduit, the total volume of particulate matter for a given time period is determined by monitoring an electrical charge built up in the probe based upon the charge of the particles flowing past the probe, wherein signals are transmitted based upon the charge of the probe. In one exemplary embodiment, a larger surface area is provided to enhance the accuracy of the probe. A controller 38 is provided for receiving the signals and determining the total amount of particulate matter that has flowed past the sensor and being collected by the emission control device, which in one non-limiting embodiment is accomplished by raising the temperature of the emission control device and/or the sensor to burn off the accumulated particulates. Once the total volume of particulate matter reaches a predetermined level, the controller initiates regeneration of the emission control device and the sensor. Thereafter, the process is repeated.

In greater detail, in one exemplary embodiment the sensor assembly 10 includes a sensing rod configured to generate signals based upon the flow of particulate matter within an exhaust gas stream. The sensing rod includes a first end having probe portion 16 configured for placement within the exhaust gas stream and for generation of the signals. The sensing rod also includes a second end configured for direct or indirect connection to electrical connector 24. The second end is further configured for engagement with one or more components of the sensor assembly such as housing 14, first insulator 22 or otherwise, for attachment of the sensing rod to the sensor assembly.

In one exemplary embodiment, the second end of the sensing rod is configured to engage the first insulator and prevent or substantially limit rotation of the sensing rod with respect to the first insulator. In one configuration, the sensor assembly includes a high temperature resistant adhesive for bonding of the second end of the sensing rod to the first insulator or other sensor assembly component. Examples of suitable high temperature adhesives include alumina based adhesives such as Ceramabond™ 571, sold by Aremco Products Inc. of Valley Cottage, N.Y. U.S.A. or equivalents thereof In another configuration, the second end of the sensor includes a corresponding shape to an opening formed in the first insulator for preventing rotation of the sensing rod with respect to the first insulator or otherwise. For example, referring to FIGS. 6A-6G, the second end of the sensing rod and opening of the first insulator includes corresponding shapes that are non-circular, oval, square, rectangular, pentagonal, hexagonal, cross or otherwise to prevent or substantially limit rotation of the sensing rod with respect to the insulator. Other configurations should be appreciated.

The probe (e.g., section of the sensing rod extending beyond the first insulator and into an exhausting gas stream) includes an overall length extending along an axis 'A' and may include a substantially consistent or varying contour, width or diameter. In one exemplary embodiment, the probe includes a length generally equal to an inner diameter of an exhaust gas conduit 36, exhaust control device 32 or otherwise. In another exemplary embodiment, the probe includes a diameter or a section having a diameter that is generally equal to an opening of an exhaust gas component configured for receiving the probe. For example, the probe (e.g., first section, second section or both) may include a maximum diameter that is between about 50%-100%, 75%-100% or 90%-100% of the diameter of the opening formed through the exhaust gas component. However, the probe may still include a diameter that is greater than an opening formed for receiving the probe but still be shaped to allow maneuvering of the probe through the opening.

Figure 2:
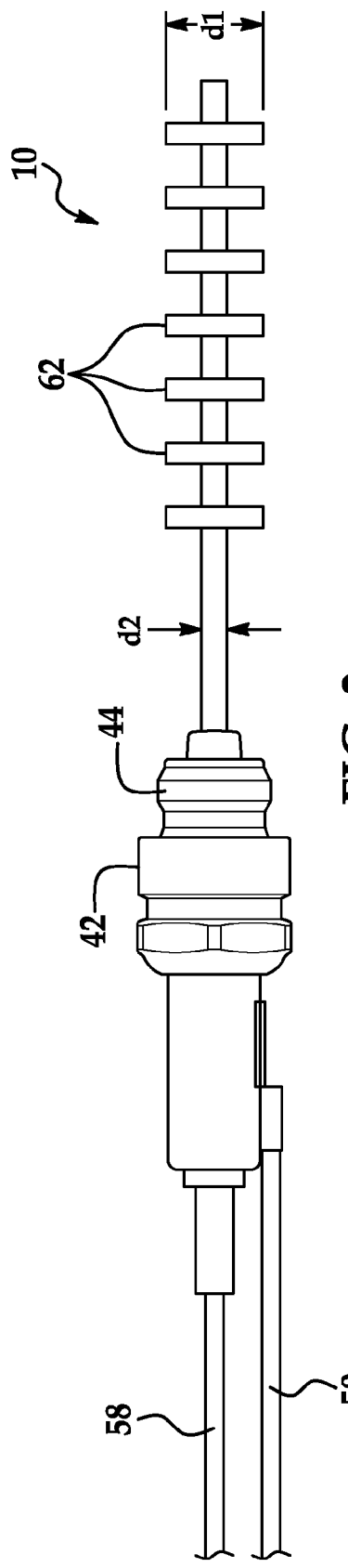
FIG. 2 illustrates an elevational view of a first exemplary embodiment of a sensor according to the teachings of the present invention.
Figure 6A:
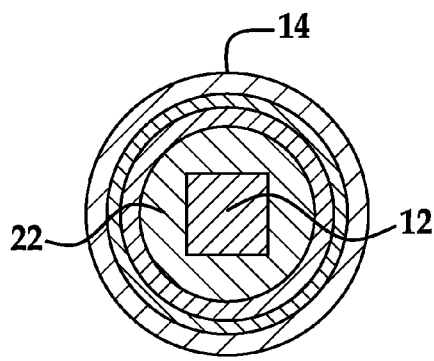
FIGS. 6A through 6G illustrate difference engagement configurations between a sensing rod and an insulator according to exemplary embodiments of the present invention.
Figure 6B:
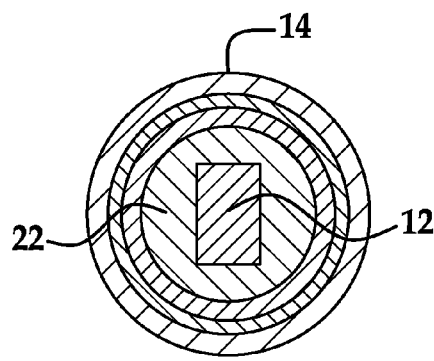
Figure 6C:
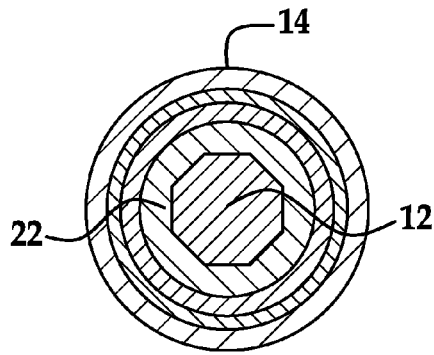
Figure 6D:
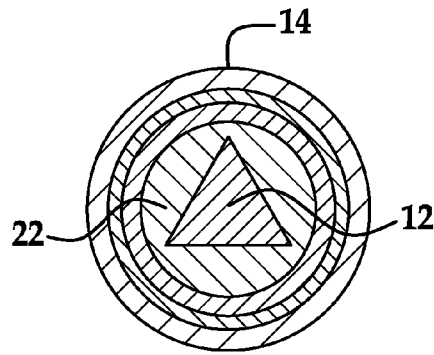
Figure 6E:
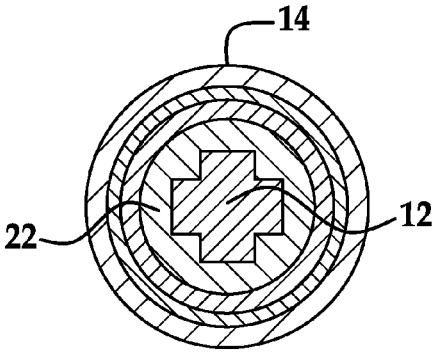
Figure 6F:
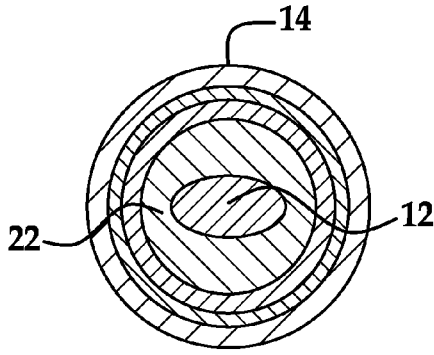
Figure 6G:
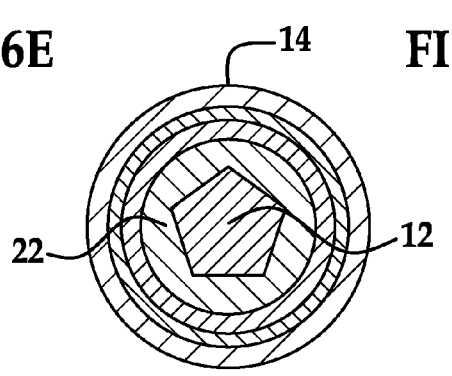

In one exemplary embodiment, by example referring to FIG. 2, the probe includes first section 18 having a maximum diameter 'd1' and second section 20 having maximum diameter 'd2'. It should be appreciate that the maximum diameter d1 may be larger or smaller than the maximum diameter of d2. However, in several exemplary embodiments, the maximum diameter d1 of the first section is greater than a maximum diameter of the second section. In certain situations, this is advantageous for creating larger surface areas for monitoring particulate matter flowing within an exhaust gas stream.

In one particular exemplary embodiment, the probe includes first section 18 having a first surface area per unit length and second section 20 having a second surface area per unit length. The first and second areas per unit length are defined as a total surface area exposed to the exhaust gas stream between two equally spaced parallel planes (or distances) of the probe. For example, referring to the schematic views of FIGS. 26 through 29, exemplary probes are shown having a first section 18 and a second section 20. Between planes A&B and C&D, which are equally spaced to form a unit length, the total surface area of the portion of the first section 18 is greater than the total surface area of the portion of the second section 20. In these configurations this is due to the larger diameter and/or shape configuration of the first section as compared to the second section. It should be appreciated that other geometries are contemplated, particularly as shown and described herein. Also, it should be appreciated that the first and second sections can be located anywhere along the length of the probe and include any unit length of measurement so long as both sections A&B and C&D are equally spaced.

As previously mentioned, in one exemplary embodiment, the surface area of the first section is greater than the surface area of the second section. It is contemplated that the surface area of the first section, or portions thereof, may at least about 1.25, 1.5, 2, 3, 4, 6, 8 or more times greater than the surface area of the second area sections per unit length. Also, it is contemplated that the first section may include a largest D1 diameter that is at least about 1.25, 1.5, 2, 3, 4 or more times greater than a largest diameter D2 of the first section.

The first and second sections of the probe may be arranged in different configurations. In one exemplary embodiment, the second section is located at a near end of the probe portion (e.g., closest to the housing) and the first portion is located at a far end of the probe portion. In this exemplary embodiment, the first section begins at a point along a length of the probe and extends to the far end of the probe opposite the housing. For example, the first portion may begin between about ¼-¾ along a length of the probe portion. As such, the first section may include a length that is greater than, less than or about equal to the length of the second section.

The first and second sections may be formed of any suitable shape for detecting particulate matter flowing within an exhaust gas stream. In one exemplary embodiment, the first and second sections are formed of different shapes. In one configuration, the second section is generally formed of a rod like member and the first section is particularly shaped and/or configured with a surface area greater than the first section, per unit length. For example, potential shapes of all or a portion of the first section include coil or helical shape, cylindrical shape, one or more (or plurality) disk shapes or members (extending radially or longitudinally along a length of the probe), one or more (or plurality) of sphere shapes or members, serrated shape or configuration (formed radially or longitudinally along a length of the probe), star cross-sectional shape (e.g., 3, 4, 5, 6, 7, 8, 9 point star or otherwise), combinations thereof or otherwise. Other shapes are available for enhancing surface area for detection of particulate matter without substantially interfering with the flow of exhaust gas.

The sensing rod may be formed of any suitable material for detection of particulate matter or other material of interest. In one configuration, the sensing rod is formed of an electrically conductive or semi-conductive material and is also capable of withstanding deleterious effects of exhaust emission (e.g., heat, corrosiveness, or otherwise). For example, the sensing rod may be formed of metal, metal alloy or otherwise. Further, as described in more detail herein, all or a portion of the sensing rod may be formed of a material particularly configured for forming an electrically or thermally insulating coating. Examples of specific suitable materials include nickel alloys such as Haynes® 214® or Haynes® 240®, both of which are sold by Haynes International Inc. of Kokomo, Ind., U.S.A. It should be appreciated that the first and second ends of the sensing rod may be formed of similar or dissimilar material. Also, the first and second sections may be formed of similar or dissimilar material.

In one exemplary embodiment, the sensing rod is formed with, generates or otherwise includes an insulating material or layer thereover to prevent transmission of electric current to or from unwanted components. This may be in addition to, or in the alternative to, any insulating material, such as first insulating material, second insulating material or otherwise. In one configuration, the insulating material or layer 27 comprises an oxide coating of a material forming the sensing rod. Suitable materials include materials capable of forming an oxide coating or layer that has low thermal and/or electrical conductivity. One exemplary material includes a first material comprising nickel alloy and a second material comprising aluminum and one or more of yttrium, zirconium or lanthanum. Other materials and combinations are possible.

In one exemplary embodiment, the sensing rod is mounted or attached to the housing through a suitable insulator, such as first insulator 22. This insulated mounting prevents current flow from the sensing rod to the housing and ultimately to an attached component, such as an exhaust system component where the signal becomes ground and hence lost. The first insulator may comprise any suitable insulating material configured to withstand temperatures encountered within an exhaust gas stream and substantially limit electrical current therethrough. Example of suitable insulating material include ceramic, glass or porcelain. The insulator is attached to the sensing rod and/or housing through a suitable adhesive. Alternatively, or in addition, the insulator is locked, restricted or otherwise trapped within the housing through a crimped portion 40 of the housing. Similarly, the electrical connector may also be mounted or attached to the housing through another or the same insulating material (e.g., first insulator 22, second insulator 26 or otherwise). It should be appreciated that attachment of the electrical connector to the housing may be achieved through the same means as attachment of the sensing rod.

As previously mentioned, the insulator for the sensing rod, electrical connector, or both, may include an opening for receiving a portion thereof In one exemplary embodiment, the opening includes a corresponding shape to that of the sensing rod or electrical connector extending therein. In another exemplary embodiment, the opening and sensing rod and/or electrical connector include a shape, such as a cross-sectional shape, that prevents or substantially limits rotation of the sensing rod and/or electrical connector with respect to the insulator, again as previously discussed. Attachment of the sensing rod and/or electrical connector to the insulator (e.g., first insulator 22, second insulator 26 or otherwise) may include an adhesive, particularly a high heat resistant adhesive for further preventing movement of the sensing rod and/or electrical connector with respect to an attached insulator.

The sensor assembly further includes housing 14 for maintaining components of the sensor assembly together and/or mounting of the sensor assembly to an exhaust component. In one exemplary embodiment, the housing comprises a shell 42. The shell includes a threaded portion 44 for mounting the sensor assembly to an exhaust component, such as an exhaust gas conduit 36, exhaust treatment device 32 or otherwise. This is achieved through engagement with a corresponding threaded component, e.g., opening, formed through the exhaust gas conduit, exhaust treatment device or otherwise. Upon engagement, probe 16 extends into an exhaust gas flow for detection of particulate matter therein. In one configuration, it is contemplated that the diameter of threaded portion 44 is generally equal to or slightly larger than the maximum diameter D1 of first section 18.

In one exemplary embodiment, as shown in FIG. 4, the housing includes a first housing portion 46 and a second housing portion 48. The first and second housing portions are configured to cover, protect and/or provide attachment for the first insulator and the second insulator. Also, the first and second housing portions provide attachment of the sensor assembly to an exhaust component. In one configuration, the first and second housing portions are attached to each other and configured to enclose the first and/or second insulator. Optionally, the housing (or first and/or second housing portions) is configured for attachment to a ground wire 50 for creating a ground for the sensor assembly.

As previously mentioned, the sensing rod is in communication with one or more additional devices for transmission of signals from the probe to another device, through electrical connector 24. In one exemplary embodiment, the sensing rod is attached directly to the electrical connector through corresponding engagement features 52, 53, respectively, such as threaded fastener, spline, crimping, welding or bonding, or otherwise. In another exemplary embodiment, the sensing rod is attached to the electric connector through a resilient intermediate connector 28, such as a coil spring or otherwise. In this configuration, the second end of the sensing rod includes a collar 54 for providing reactionary force against the resilient intermediate connector. Similarly, the electrical connector also includes a collar 56 for providing reactionary force against the resilient intermediate connector. Other configurations are contemplated.

The electric connector is configured for providing communication between the sensing rod and another device, such as controller 38. The electric connector is configured for attachment or electrical coupling with the sensing rod and another device. In one configuration, the electric connector is attached or in electrical communication to another device through a signal wire 58 or the like. Attachment of the electric connector to the wire may be achieved through any suitable means. In one exemplary embodiment, attachment of the electrical connector to the wire is achieved through crimping of a first end of the electrical connector to the wire. In another exemplary embodiment, the electric connector forms an attachment feature 60 configured to engage a corresponding attachment features formed or attached to the wire. With respect to connection of the electric connector to the sensing rod, in one exemplary embodiment, the electrical connector is directly attached to the sensing rod. Attachment of the electrical connector directly to the sensing rod may be improved upon through the use of high temperature resistant conductive adhesives, mechanical engagement features (e.g., corresponding threaded components) or otherwise. Alternatively, in another exemplary embodiment, and as previously discussed, the electrical connector may be in electrical communication with the sensing rod through intermediate connector 28 and more particularly, in one configuration, a coil spring.

In one configuration the sensor assembly is in communication with controller 38 for example, a controller for an exhaust treatment system. In an alternative embodiment, the controller is part of an electronic control unit of a vehicle. In either of these configurations, the control unit is configured to transmit and receive signals from the sensor. Such information is particularly advantageous for determining the amount of particulate matter that has flowed through the emission control device in a given time period or cycle interval such as between regenerations of the emission control device, particulate matter sensor or both. Accordingly and in one configuration, the controller may cause regeneration of the exhaust control unit and/or sensor based upon the particulate matter flowing within the exhaust gas as indicated by the sensor assembly.

The sensor assembly may be used in various industries for determining a flow of particulate matter. These industries include, without limitation, automotive industry, freight industry, mass transit industry, power generating industry such as power plants or factors, or other emission producing industry. In one particularly advantageous application, the sensor assembly is useable within the automotive industry and more particularly with internal combustion engines of vehicles for monitor particulate matter generated thereby. In this configuration, the sensor assembly may be place within the exhaust gas stream flowing through an exhaust gas conduit, exhaust treatment device or otherwise, from a diesel engine, gasoline engine or otherwise.

In view of the foregoing, FIGS. 2-5 and 7-25 illustrate other exemplary embodiments of various sensor assembly configurations. It should be appreciated that the features of these embodiments may incorporated into any other embodiment and thus should not be considered limiting to the specific embodiment in which the feature is shown.

Referring to FIGS. 2-4, a first exemplary embodiment of a sensor assembly 10 is shown. In this embodiment, the sensor assembly includes a sensing rod 12 having probe 16 which includes a first section 18 and a second section 20, the first section including at least a portion having a greater surface area per unit length than the second section. The first section includes a plurality of disks 62 extending from the probe. The disks are orientated in the direction of anticipated exhaust gas flow and perpendicular with respect to a length of the probe. The sensor rod is partially housed within first housing portion 46 and separated from the first housing portion through first insulator 22. The first housing portion includes threaded portion 44 for attachment to exhaust gas conduit 36 or exhaust treatment device 32. The sensor rod is in communication with electrical connector 24 through intermediate connector 28 and more specifically a coil spring. The sensor rod and electrical connector both includes respective collars 54, 56 for engaging the coil spring and limiting lateral movement of the coil spring. The electrical connector is housed within second housing portion 48 and adapted for communication with a controller through signal wire 58. The first and second housing portions are configured to provide reactionary counter forces to the sensing rod and electrical connector as a result of intermediate force applied by the coil spring connector. The electrical connector is attached to the wire through crimping means.

Referring to FIG. 5, a second exemplary embodiment of a sensor assembly 10 is shown, which is a variant of the first exemplary embodiment and includes similar features thereof In this embodiment, probe 16 of the sensing rod 12 is substantially straight. Additionally, with respect to both the first and second embodiments, or even any embodiment shown or described herein, engagement of the sensing rod with the first insulator is improved upon with the use of heat resistant adhesive and/or one of the engagement configurations shown in FIGS. 6A-6G.

Figure 7:
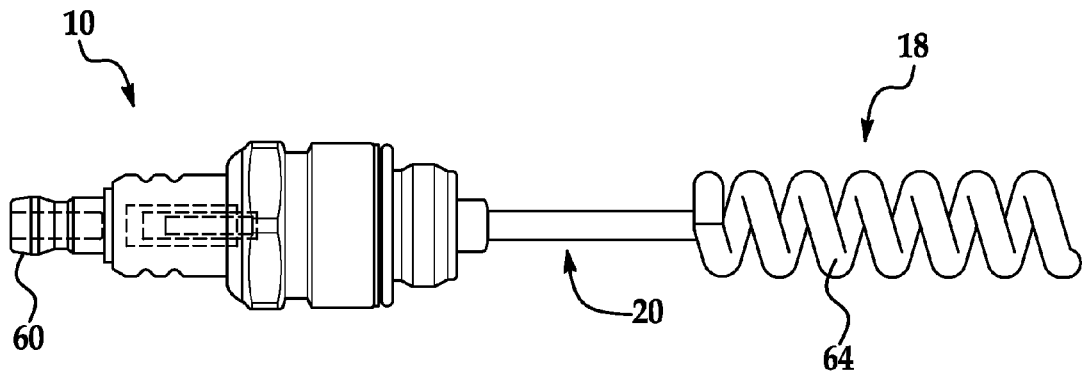
FIG. 7 illustrates an elevational view of a second exemplary embodiment of a sensor according to the teachings of the present invention.
Figure 8:
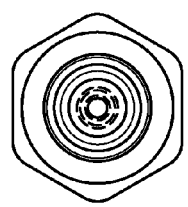
FIG. 8 illustrates an end view of the sensor shown in FIG. 7.
Figure 9:
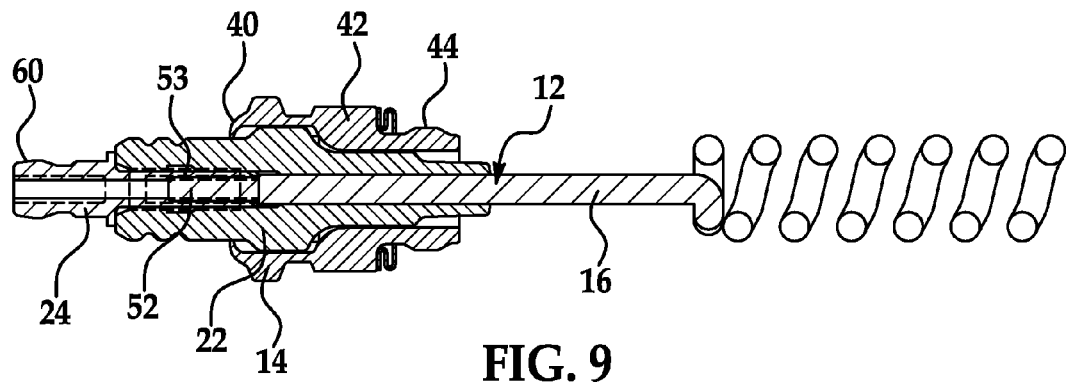
FIG. 9 illustrates a cross sectional view of the sensor shown in FIG. 7.

Referring to FIGS. 7-9, a third exemplary embodiment of a sensor assembly is shown. In this embodiment, the sensor includes a sensing rod 12 having probe 16 that includes a first section 18 and a second section 20, the first section including at least a portion having a greater surface area per unit length than the second section. The first section is formed of coils 64 arranged in a helical pattern extending to the end of the probe. The coils forming the helical pattern are spaced apart to allow fluid flow (e.g., exhaust gas) therethrough. The sensor rod is partially housed within housing 14 and separated from the housing through insulator 22. The housing includes threaded portion 44 for attachment to exhaust gas conduit 36 or exhaust treatment device 32. The sensor rod is in direct contact and communication with electrical connector 24 through corresponding engagement features 52, 53. The electrical connector is also housed within insulator 22 and adapted for communication with a controller through a suitable connector.

Figure 10:
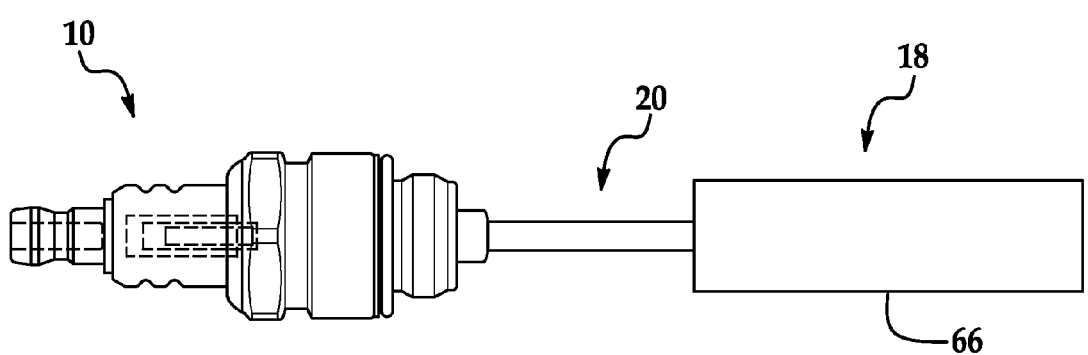
FIG. 10 illustrates an elevational view of a third exemplary embodiment of a sensor according to the teachings of the present invention.
Figure 11:
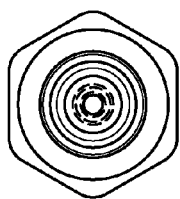
FIG. 11 illustrates an end view of the sensor shown in FIG. 10.
Figure 12:
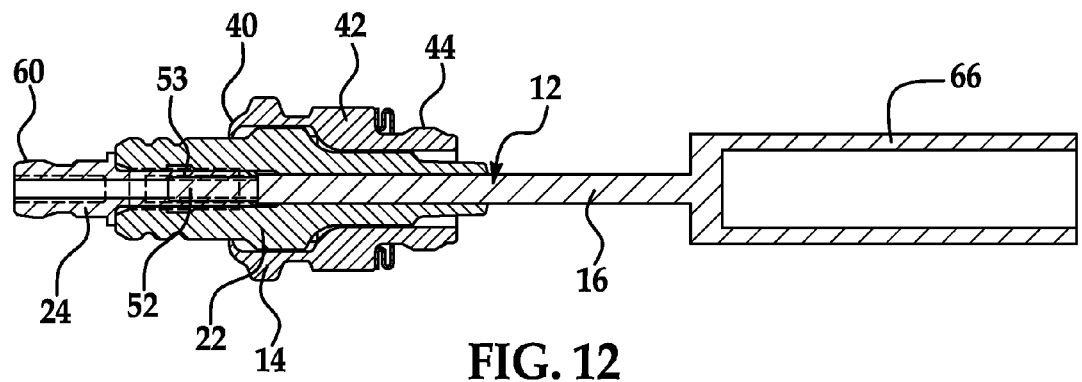
FIG. 12 illustrates a cross sectional view of the sensor shown in FIG. 10.

Referring to FIGS. 10-12, a fourth exemplary embodiment of a sensor assembly is shown. In this embodiment, the sensor includes a sensing rod 12 having probe 16 that includes a first section 18 and a second section 20, the first section including at least a portion having a greater surface area per unit length than the second section. The first section is formed of a hollow cylindrical member 66 extending to the end of the probe. The sensor rod is partially housed within housing 14 and separated from the housing through insulator 22. The housing includes threaded portion 44 for attachment to exhaust gas conduit 36 or exhaust treatment device 32. The sensor rod is in direct contact and communication with electrical connector 24 through corresponding engagement features 52, 53. The electrical connector is also housed within insulator 22 and adapted for communication with a controller through a suitable connector.

Figure 13:
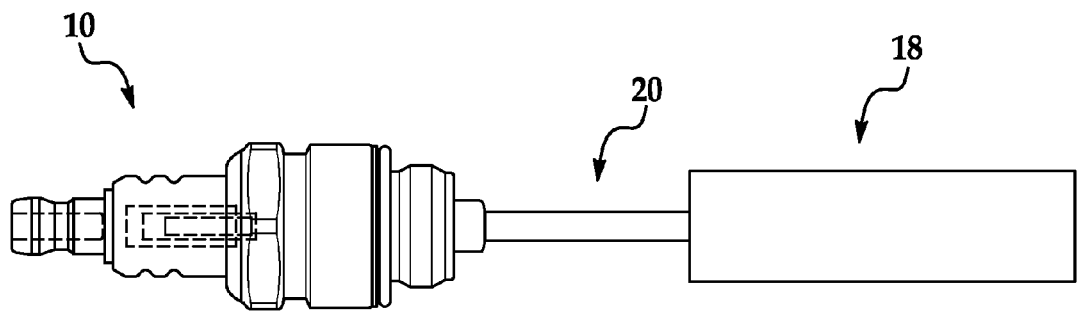
FIG. 13 illustrates an elevational view of a forth exemplary embodiment of a sensor according to the teachings of the present invention.
Figure 14:
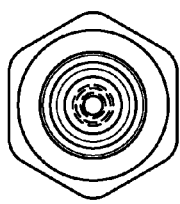
FIG. 14 illustrates an end view of the sensor shown in FIG. 13.
Figure 15:
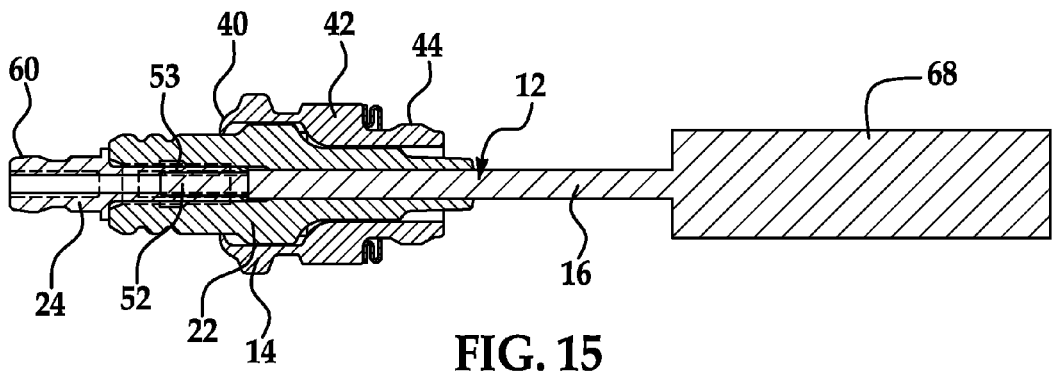
FIG. 15 illustrates a cross sectional view of the sensor shown in FIG. 13.
Figure 16:
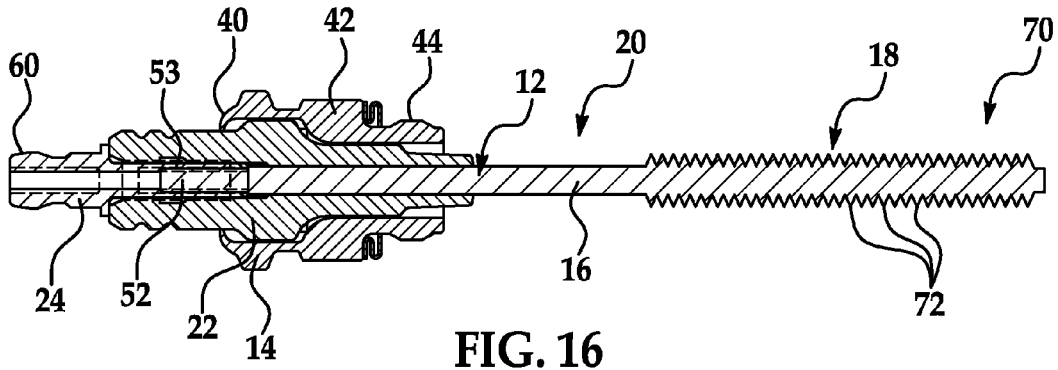
FIG. 16 illustrates a cross sectional view of a fifth exemplary embodiment of a sensor according to the teachings of the present invention.
Figure 17:
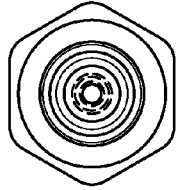
FIG. 17 illustrates an end view of the sensor shown in FIG. 16.
Figure 18:
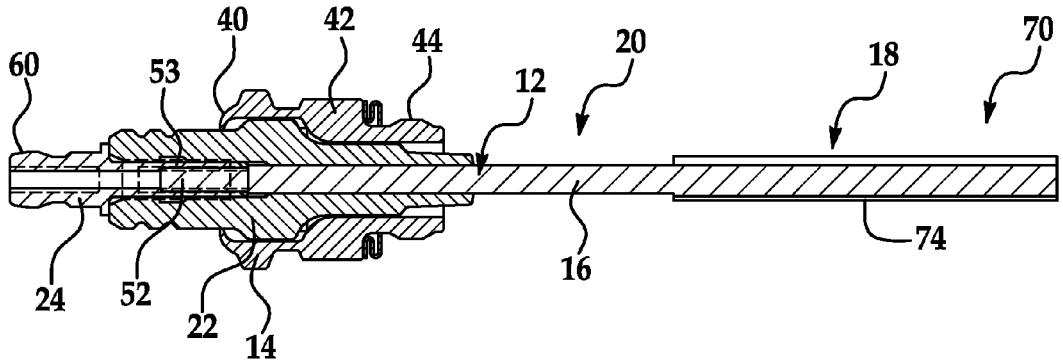
FIG. 18 illustrates a cross sectional view of a sixth exemplary embodiment of a sensor according to the teachings of the present invention.
Figure 19:
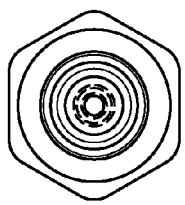
FIG. 19 illustrates an end view of the sensor shown in FIG. 18.
Figure 20:
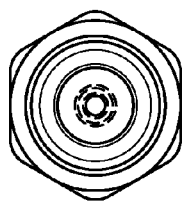
FIG. 20 illustrates another end view of the sensor shown in FIG. 18.
Figure 21:
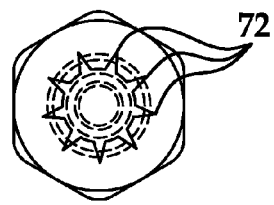
FIG. 21 illustrates an enlarged view of a sensing rod shown in FIG. 20.
Figure 22:
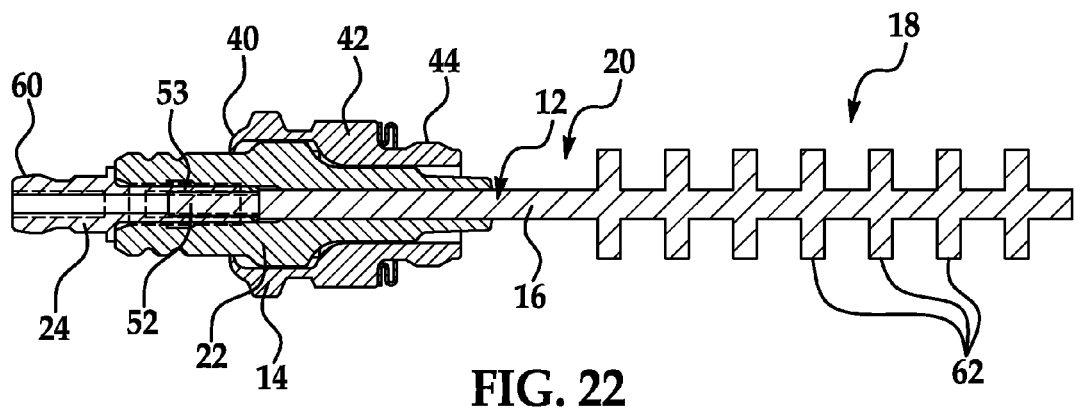
FIG. 22 illustrates a cross sectional view of a seventh exemplary embodiment of a sensor according to the teachings of the present invention.
Figure 23:
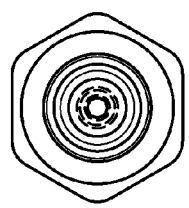
FIG. 23 illustrates an end view of the sensor shown in FIG. 22.

Referring to FIGS. 13-15, a fifth exemplary embodiment of a sensor assembly is shown, which is a variant of the fourth exemplary embodiment and includes similar features thereof In this embodiment, probe 16 of the sensing rod 12 includes a solid cylindrical member 68.

Referring to FIGS. 16-21, a sixth and a seventh exemplary embodiment of a sensor assembly is shown. In these embodiments, the sensor assemblies include a sensing rod 12 having probe 16 that includes a first section 18 and a second section 20, the first section including at least a portion having a greater surface area per unit length than the second section. The first section is formed of a serrated member 70 extending to the end of the probe. With reference to the exemplary embodiment shown in FIGS. 16 and 17, the serrated member includes serrated portions 72 disposed along the length of the probe and extending radially about the probe in a rotational direction perpendicular to the length of the probe. With reference to the exemplary embodiment shown in FIGS. 18-21, the serrated member includes serrated portions 74 disposed about a radius of the probe and extending along the length of the probe. The sensor rod is partially housed within housing 14 and separated from the housing through insulator 22. The housing includes threaded portion 44 for attachment to exhaust gas conduit 36 or exhaust treatment device 32. The sensor rod is in direct contact and communication with electrical connector 24 through corresponding engagement features 52, 53. The electrical connector is also housed within insulator 22 and adapted for communication with a controller through a suitable connector.

Referring to FIGS. 22-25, an eighth and a ninth exemplary embodiment of a sensor assembly is shown. In these configurations, the sensor includes a sensing rod 12 having probe 16 that includes a first section 18 and a second section 20, the first section including at least a portion having a greater surface area per unit length than the second section. With reference to the exemplary embodiment shown in FIGS. 22 and 23, the first section includes a plurality of disks 62 extending from the probe. The disks are orientated in the direction of anticipated exhaust gas flow and perpendicular with respect to a length of the probe. With reference to the exemplary embodiment shown in FIGS. 24 and 25, the first section includes a plurality of spherical members 74 disposed along the length of the probe. The sensor rod is partially housed within housing 14 and separated from the housing through insulator 22. The housing includes threaded portion 44 for attachment to exhaust gas conduit 36 or exhaust treatment device 32. The sensor rod is in direct contact and communication with electrical connector 24 through corresponding engagement features 52, 53. The electrical connector is also housed within insulator 22 and adapted for communication with a controller through a suitable connector.

With reference to the embodiments shown in FIGS. 2-5 and 7-25 and otherwise shown or described herein, it should be appreciated that these and other configurations may include a sensor rod formed of a material configured to oxide to develop a layer of substantially low electrical conductivity. This is particularly advantageous for insulating the sensing rod from the housing or other component. For example, as previously described, the sensor assembly may include a sensing rod formed of a first material comprising nickel alloy and a second material comprising aluminum and one or more of yttrium, zirconium or lanthanum.

Exemplary embodiments of the present invention also include methods for determining flow rate of particulate matter through an exhaust component of an engine. The method includes placing a particulate matter sensor in an exhaust gas stream of an internal combustion engine. The particulate matter sensor comprises any of the particulate matter sensors described or shown herein. The method further includes generating signals with the particulate matter sensor based upon the presence of particulate matter flowing in the exhaust gas stream and flowing past the sensor. As previously mentioned and in one exemplary embodiment, the signal is based upon a charge created in the probe based upon particulate matter flowing past the sensor, wherein larger surface area configurations enhance the accuracy of the probe. The controller receives the signals and determines at least one flow characteristic of particulate matter flowing within the exhaust gas stream such as total amount of particulate matter flowing by the sensor and into the emission control device, or volume flow rate of particulate matter or otherwise. With this information the controller can determine when regeneration of the sensor and/or emission control devices is necessary. Also, the control device may further initiate such regeneration according to suitable means within the art.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiments disclosed as the best mode contemplated for carrying out this invention, but that the invention will include all embodiments falling within the scope of the present application.

What is claimed is:

1. A sensor for detecting and monitoring particulate matter within an exhaust gas flow path of an engine, the sensor comprising:

a housing including an attachment feature for mounting the sensor;

a sensing rod supported by an insulator disposed within the housing, the sensing rod being attached to the insulator and including a probe adapted to be placed within the exhaust gas flow path, the sensing rod being configured to detect an amount of particulate matter that has flowed through the exhaust component and generate signals based thereupon;

an electrical connector in communication with the sensing rod, the electrical connector being configured to transmit the signal generated by the sensing rod to a controller;

a coil spring in direct contact with the sensing rod and the electrical connector for providing electrical communication therebetween, wherein the sensing rod includes a stepped collar for engaging the coil spring and the electrical connector includes a stepped collar for engaging the coil spring; and wherein the sensing rod includes an electrically insulating layer comprising an oxide coating formed over the sensing rod, the electrically insulating layer providing electrical insulation between the sensing rod and the housing; and the probe includes a section having an increased surface area per unit length as compared to at least one other section of the probe.

2. The sensor of claim 1, wherein the configuration of the stepped collar of the sensing rod or the electrical connector is anyone of square, rectangle, octagon, triangle, cross, oval or pentagon.

3. The sensor of claim 2, wherein the insulator is configured to have a corresponding shape to the stepped collar to prevent rotation of the sensing rod with respect to the insulator.

4. The sensor of claim 1, wherein the sensing rod is bonded to the insulator with a cement or high temperature resistant adhesive.

5. The sensor of claim 1, wherein the section having the increased surface area is formed by a plurality of coils in a helical shape.

6. The sensor of claim 1, wherein the section having the increased surface area is cylindrical in shape and includes an outer diameter greater than an outer diameter of the at least one other section of the probe.

7. The sensor of claim 1, wherein the section having the increased surface area is defined by a plurality of serrations.

8. The sensor of claim 1, wherein the section having the increased surface area is defined by a plurality of spheres or a plurality of disks located along a length of the probe.

9. The sensor of claim 1, wherein the sensing rod is formed of a nickel alloy and any one of aluminum, yttrium, zirconium, lanthanum or combinations thereof.

10. The sensor of claim 1, wherein a distal end portion of the coil spring surrounds a distal end portion of the sensing rod.

* * * * *